United States Patent
Scheller et al.

(10) Patent No.: US 6,575,989 B1
(45) Date of Patent: Jun. 10, 2003

(54) ADJUSTABLE STIFFNESS MEMBRANE SCRAPER

(75) Inventors: Gregg D. Scheller, Chesterfield, MO (US); Michael D. Auld, Chesterfield, MO (US); Christopher F. Lumpkin, O'Fallon, MO (US)

(73) Assignee: Synergetics, Inc., St. Charles, MO (US)

( * ) Notice: Subject to any disclaimer, the term of this patent is extended or adjusted under 35 U.S.C. 154(b) by 171 days.

(21) Appl. No.: 09/659,099

(22) Filed: Sep. 11, 2000

Related U.S. Application Data

(60) Provisional application No. 60/153,574, filed on Sep. 13, 1999.

(51) Int. Cl.$^7$ .................................................. A61B 17/24
(52) U.S. Cl. ...................................................... 606/161
(58) Field of Search .............................. 606/1, 16, 161, 606/131, 107, 159, 162; 600/156, 20

(56) References Cited

U.S. PATENT DOCUMENTS

| | | |
|---|---|---|
| 2,617,420 A | 11/1952 | Jozefczyk et al. |
| 3,809,101 A | 5/1974 | Shimizu |
| 4,285,072 A | 8/1981 | Morcher et al. |
| 4,537,193 A | 8/1985 | Tanner |
| 4,909,784 A | 3/1990 | Dubroff |
| 5,078,712 A | 1/1992 | Easley et al. |
| 5,112,328 A | 5/1992 | Taboada et al. |
| 5,157,603 A | 10/1992 | Scheller et al. |
| 5,201,730 A | 4/1993 | Easley et al. |
| 5,275,593 A | 1/1994 | Easley et al. |
| 5,318,560 A | 6/1994 | Blount et al. |
| 5,356,407 A | 10/1994 | Easley et al. |
| 5,370,658 A | 12/1994 | Scheller et al. |
| 5,437,754 A | 8/1995 | Calhoun |
| 5,441,496 A | 8/1995 | Easley et al. |
| 5,554,155 A | 9/1996 | Awh et al. |
| 5,562,691 A | 10/1996 | Tano et al. |
| 5,603,710 A | 2/1997 | Easley et al. |
| 5,681,264 A | 10/1997 | Ryan, Jr. |
| 5,735,793 A | 4/1998 | Takahashi et al. |
| 5,785,645 A | 7/1998 | Scheller |
| 5,893,877 A | 4/1999 | Gampp, Jr. et al. |
| 5,921,998 A | 7/1999 | Tano et al. |
| 5,993,072 A | 11/1999 | de Juan, Jr. et al. |

Primary Examiner—Danny Worrell
(74) Attorney, Agent, or Firm—Thompson Coburn LLP

(57) ABSTRACT

A microsurgical instrument used in ophthalmic surgery to remove proliferative membranes during a surgical procedure treating proliferative vitreoretinal membrane disorders and other macular diseases where the microsurgical instrument has a instrument handle, a tip, and abrasive particles attached to a scraping edge projecting beyond the tip. The microsurgical instrument may be fitted with infusion, aspiration, or illumination sources, and these sources are directed to the surgical site in proximity to the scraping edge, the abrasive particles on the edge scrape membranes to remove tissue at the surgical site. In one embodiment, the microsurgical instrument may be configured with a retractable/extendable pick where the relative stiffness of the pick and the edge may be adjusted. In another embodiment the edge may also be angularly positionable as it is retracted/extended from the microsurgical instrument.

20 Claims, 2 Drawing Sheets

ADJUSTABLE STIFFNESS MEMBRANE SCRAPER

This application is a continuation of provisional patent application serial No. 60/153,574 filed Sep. 13, 1999, presently pending.

BACKGROUND OF THE INVENTION

1. Field of the Invention

The present invention relates to a type of microsurgical instrument used in treatment of intraocular diseases such as proliferative vitreoreitnal disorders. The microsurgical tool may be configured to provide the surgeon with improved methods for the removal of proliferative membranes from the surface of the retina or for the removal of residual cortical vitreous proliferative membranes from the areas surrounding the macular hole.

2. Description of the Background

Proliferative vitreoretinal disorders are manifested in the intraocular cavity of the eye by the growth of proliferative membranes on the neurosensory retina. In the conventional treatment for vitreoretinal disorders, the membranes are removed from the neurosensory membranes with various microsurgical instruments such as intraocular forceps and intraocular picks. The microsurgical instruments are introduced into the intraocular cavity through an incision in the eye, and the membranes are carefully removed from the neurosensory surface of the retina without causing tears or hemorrhages.

Depending on the stage of the disorder and the growth of the membranes, the membranes have a different texture and composition. Mature membranes tend to be removed with less complication when compared with the removal of immature membranes. With conventional intraocular forceps and picks, the surgeon is generally able to remove mature membranes from the surface of the retina as a film. When the mature membranes are removed as a film, more complete removal from the surface of the retina is possible with a lower chance of membranes remaining on the surface. On the other hand, immature membranes tend to be friable in nature because they have not acquired the necessary cross-section to be removed with conventional intraocular picks and intraocular forceps. Being friable in texture, the immature membranes do not peel of as a film, and consequently, immature membranes, which are not fully removed during surgery, may be a nidus for future membrane formation, causing the patient to undergo future operations for removal of these membrane formations.

A recent invention, effective in the treatment of proliferative vitreoretinal disorders, has been developed to mechanically remove mature and immature proliferative membranes from the neurosensory surface of the retina without the use of intraocular picks or intraocular forceps. This invention described by Tano, et al. (U.S. Pat. No. 5,921,998 ('998), incorporated herein by reference) uses an abrasive media on a tip of the microsurgical instrument to scrape the membranes from the surface of the retina. The advantages of this invention are a reduced chance of retinal tearing and hemorrhaging and the ability to remove membranes despite the stage of the growth of the membrane.

The abrasive media of the '998 instrument is affixed on the distal end of a straight probe. The straight probe is introduced into the eye through a cannula that is inserted through an incision into the intraocular cavity in the eye. The abrasive media described in the '998 patent may be diamond, silicone carbide, quartz, or alumina. The abrasive particles are biologically inert and bonded to the distal end of the probe in a manner such that the shedding of particle into the retinal tissue is avoided. By using different instruments having tips with varying types of abrasive particles, it is possible for the surgeon to more carefully separate and remove these proliferative membranes from the retina without causing damage to the retina. The removal rate may be varied depending upon the type of particles that are bonded to the tip of the microsurgical instrument, where the rate of tissue removal is in proportion to the coarseness of the particles bonded to the tip. The surgeon may more carefully control the removal rate of the proliferative membranes ensuring retinal tears and other damage to the retina does not occur, in distinction to other methods that use intraocular picks and forceps to remove the proliferative membranes.

During surgery for the treatment of vitreoretinal disorders, the surgeon may use in conjunction with these previously mentioned surgical instruments other more common surgical instruments to execute the other functions required during the operation. These microsurgical instruments are also introduced into the intraocular cavity through the cannula. A common instrument is one that is designed to deliver an aspiration source locally to an area to remove tissue. Another common instrument is used to provide infusion to the surgical area for irrigation and flushing as required. The surgeon may use a combination of these instruments and techniques to condition the surface of the retina and remove membranes by the devices previously mentioned. In some conventional instruments, a single instrument capable of performing both of these functions has been used to perform both aspiration and infusion functions.

Other common instruments aid in the visualization of the surgical site. Often the surgeon wishes to illuminate the surgical site or surface of the retina for more complete visualization of the membranes. In conventional instruments, the surgical site may be illuminated or visualized by a fiber optic cable fitted into a probe that is inserted through the cannula into the eye. The fiber optic cable may also be fitted onto a conventional probe to transmit a video picture signal back to a display to give the surgeon a visual image of the surgical site on the surface of the retina. This enhanced visual representation of the surface of the retina allows the surgeon to evaluate the operation and to more completely remove the proliferative membranes during the operation.

Generally, during the course of the operation, the surgeon must alternate between probes to carry out the specific function required at a particular stage of the operation. When changing probes, the old probe must be removed from the cannula and a new probe must be inserted. Generally, the type of cannula used is either straight or curved depending upon the instruments to be used during the surgery and the location of the surgical site in relation to the incision site. Curved probes cannot be inserted through straight cannulas, and straight probes cannot be inserted through curved cannulas. In a surgical procedure using these conventional instruments, the surgeon must make an initial choice to the style or cannula and instrument to be used during the operation.

Sometimes, the surgeon will find that during the course of the operation, a surgical instrument having a straight probe will not efficiently deliver aspiration or infusion to the target area. This may be due to the positioning of the incision or instrument entry site in the eye relative to the target surgical site. The surgeon may decide that a curved probe would provide better range to deliver infusion or aspiration to the surgical site. This change also requires a change in the style of cannula or the use of the probe through the eye incision itself. Such a changeover complicates the operation and often produces additional and sometimes harmful stresses on the eye. Similarly, the delivery of the optical fiber to the surgical site is generally through a straight probe so that the surgeon may directly visualize or illuminate the affected area. Curved probes may also be used with curved cannulas that are aimed to the surgical site. The changeover also complicates the operation and often produces additional and sometimes harmful stresses on the eye.

To overcome these disadvantages of prior art microsurgical instruments used during ophthalmic surgical operations, what is needed is a microsurgical instrument, which combines the functions of infusion and aspiration with abrasive membrane scraping or the functions of illumination with abrasive membrane scraping. The invention could be provided in an adjustable curved member that is adaptable to a straight cannula, thus providing the surgeon with increased range for membrane scraping. The invention could also be provided in a pick and scraping device that could increase the versatility of the instrument introduced to the surgical site. Such an invention would thereby increase the likelihood of success of an operation for removal of vitreoretinal proliferative membrane disorders and other intraocular diseases without undue stress on the tissue surrounding the entry incision.

SUMMARY OF THE INVENTION

The microsurgical instrument of the present invention allows the surgeon to treat proliferative vitreoretinal membrane disorders more effectively with less chance of hemorrhaging and tearing. The microsurgical instrument of the present invention combines the advantages of abrasive membrane scraping with the features of aspiration/infusion, and the advantages of abrasive membrane scraping with illumination. In the preferred embodiments of the invention, the microsurgical tool is configured with abrasive particles that are made from synthetic diamond. The diamond particles are preferably contained on a film that is bonded to the distal end portion of the microsurgical instrument. The microsurgical instrument may then be introduced into the intraocular cavity through a straight cannula inserted in through an incision in the eye.

In one embodiment of the apparatus of the invention, the illuminated diamond dusted membrane scraper, the microsurgical instrument has the ability to scrape the membrane surface while providing illumination of the surface to be treated. In this embodiment the apparatus of the invention includes an instrument handle, a tip extending outward and away from the instrument handle, and an adapter fitted onto a distal end of the tip. Preferably, the adapter is cylindrical in shape and has a bevel section-cut across its outside cylindrical surfaces. The abrasive particles are bonded to the outermost tip of the adapter. The instrument handle, tip, and adapter have hollow interiors that are configured to receive and encase an optical fiber. The optical fiber is capable of transmitting/receiving visual imagery or providing illumination. The optical fiber may be positioned through the bevel section-cut in the adapter to illuminate the adapter or transmit/receive visual images of the surgical site. Preferably, the adapter is a flexible and translucent member to facilitate scraping and transillumination.

The second embodiment of the present invention, the illuminated diamond dusted membrane scraper, is similarly constructed. In this embodiment of the invention, the microsurgical instrument includes an instrument handle and a tip extending outward and away from the instrument handle. The instrument handle and tip have a hollow interior; however, in this configuration, the adapter is affixed to a bracket connected to the distal end of the tip, and the adapter is positioned at an acute angle to the tip with the adapter distal end projecting away from the tip distal end. The abrasive particles are deposited on the outermost edge of the adapter. The optical fiber is positioned in the hollow interior of the instrument handle and the tip such that the operative end of the optical fiber is positioned at the distal end of the tip. In this configuration, the optical fiber may illuminate the surgical site or transmit/receive visual imagery of the surgical site. The path of transmission/receipt from the optical fiber intersects the adapter distal end. The surgical site may be illuminated or visualized directly while the surface is scraped by the adapter.

An additional embodiment of the apparatus of the invention has the ability to scrape membranes, while providing infusion or aspiration to the surgical site. In this configuration the microsurgical instrument includes an instrument handle, a tip extending outward and away from the instrument handle, and an adapter fitter on the distal end of the tip. The abrasive particles are contained on the adapter. The instrument handle, tip and adapter have hollow interiors. The hollow interior of the instrument handle may be configured to accept an interface from an external infusion source or an aspiration source. The microsurgical instrument may be introduced into the intraocular cavity, and the adapter may be used to scrape the retinal surfaces. The hollow interiors of the instrument handler, tip and adapter form a channel inside the microsurgical instrument to deliver infusion/aspiration functions to the surgical site.

In another embodiment of the apparatus of the invention, a diamond dusted membrane scraper having a pick with an adjustable stiffness is provided. In this embodiment of the invention, the microsurgical instrument includes an instrument handle, a tip extending outward and away from the instrument handle and an adapter fitted onto the tip. The instrument handle, tip, and adapter have hollow interiors that are configured receive and encase a pick that may be retracted or extended from a hole in the outermost end of the adapter. The pick has a relative stiffness that is indirectly proportional to a length of the pick exposed from the outermost end of the adapter. When the length of the exposed pick is increased, the stiffness of the pick decreases. The stiffness of the pick is adjustable through a control mechanism on the instrument handle that adjusts the length of the pick exposed from the outermost end of the adapter. The amount of stiffness of the pick is controlled by the surgeon to allow the surgeon more flexibility in removing membranes affixed to the surface of the retina. The pick may be fully retracted into the hollow interior of the microsurgical instrument so that the surgeon may utilize the scraping capability provided by abrasive particles deposited on the adapter. The surgeon may also vary the relative stiffness of the adapter by controlling the length of the pick retained in a portion of the hollow interior of the adapter.

In a similar embodiment of the apparatus of the invention, a directional endoscopic abrasive aspiration instrument is provided. In this embodiment of the invention, the microsurgical instrument includes an instrument handle and a tip extending outward and away from the instrument handle. The instrument handle and tip have hollow interiors that are configured to receive and encase a tube that may be retracted or extended from a hole in the distal end of the tip. The extension of the tube is adjustable through a control mechanism on the instrument handle that adjusts the length of tube exposed from the outermost end of the tip. Abrasive particles are deposited on the exterior of the tube at its distal end. Preferably, an elastic nitinol tube is used and pre-formed with a curved distal end. The curvature of the tube may be controlled by controlling the length of tube that is retracted or extended from the tip. In the fully retracted position, the tube is fully contained within the tip and may be inserted into a straight cannula into the incision in the eye. When inside the eye cavity, the tube may be extended from the tip allowing the tube to bend and curve to reach areas that may have been unreachable by a straight instrument. The hollow interior of the instrument handle may be configured to accept an external device to provide aspiration/infusion functions at the distal end of the tube. Simultaneously, the surgeon may remove membranes by scraping the retinal surfaces with the distal end of the tube. The retinal surfaces may be conditioned as required through infusion and tissue may be removed through aspiration.

With the constructions and arrangements of the ophthalmic microsurgical tools mentioned above, it is possible to more effectively remove the vitreoretinal proliferative membranes without excessive damage to the retina and without undue stress to the entry incision into the intraocular cavity.

BRIEF DESCRIPTION OF SEVERAL VIEWS OF THE DRAWINGS

Further objectives and features of the invention are revealed in the following detailed description of the preferred embodiment of the invention and in the drawing figures wherein.

Corresponding reference characters indicate corresponding parts throughout the several views of the drawings.

DETAILED DESCRIPTION OF THE INVENTION

Figure 1A:
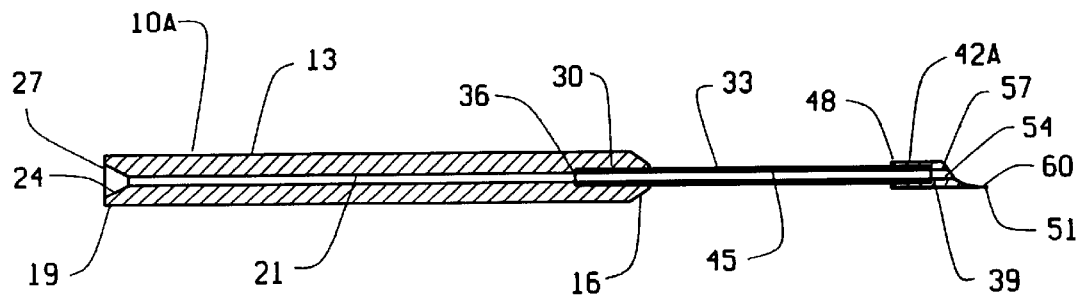
FIG. 1A is cross sectional view of one embodiment of the present invention, an infusion/aspirating diamond dusted membrane scraper.

FIG. 1A shows one embodiment of the apparatus of the present invention, an infusion and aspiration microsurgical instrument. The microsurgical instrument 10A consists of an instrument handle 13 with opposite distal 16 and proximal ends 19. The instrument handle 13 is a hollow cylinder arranged with an internal passage 21 running through its center axis. The instrument handle 13 may be disposable or re-useable, and is to be constructed from light-weight material compatible with common sterilization processes. The internal passage 21 provides communication between the opposite proximal 19 and distal 16 ends. At the proximal end 19 of the instrument handle 13, the internal passage 21 is outwardly and frustoconically shaped to create a luer taper 24 for attachment to external aspiration or infusion sources 27. Preferably, the distal end 16 of the instrument handle 13 has a counter bore 30, and the diameter of the counter bore 30 is dimensioned so that the tip 33 may be securely press fit into the instrument handle 13. The length of the counter bore 30 is set to provide minimum deflection of the tip 33 and to anchor the tip 33 to the instrument handle 13. However, other methods of attaching the tip 33 to the instrument may be used. Additionally, it is possible to form the instrument handle and the tip as a monolithic unit to avoid the need to firmly secure the tip to the instrument handle.

The tip 33 is a tube with opposite proximal and distal ends 36, 39. Preferably, the tip 33 is made from a stainless steel hypodermic tube. The tip 33 is attached to the instrument handle 13 by inserting and adhering a proximal end 36 of the tip in the counter bore 30 on the instrument handle 13 such that the distal 39 end extends outward and away from the instrument handle 13. The distal end 39 of the tip is configured to accept an adapter 42A. The tip 33 has a hollow core 45 that allow communication into the internal passage 21 of the instrument handle 13. Preferably, the diameter of the hollow core 45 matches the diameter of the handle internal passage 21 to allow the smooth flow of liquid through the instrument handle 13 to the tip 33 of the microsurgical instrument 10A.

As shown in FIG. 1A, the distal end 39 of the tip is provided with the adapter 42A. Preferably, the adapter 42A is a cylindrically shaped member having proximal and distal ends 48, 51 and an internal chamber 54 running between proximal and distal ends 48, 51. The internal chamber 54 provides communication from the distal end 51 of the adapter 42A into the hollow core 45 of the tip 33 and into the internal passage 21 of the instrument handle 13. Preferably, the portion of the internal chamber 54 at the proximal end 48 of the adapter 42A is configured to slide over the exterior of the distal end 39 of the tip 33 and securely seat on the tip 33. Preferably, the adapter 42A is elastic and expands to fit over the distal end of the tip 33 and is adhered in place. To maintain the flexibility of the adapter 42A during scraping the distal end 39 of the tip 33 is only partially inserted into the internal chamber 54 of the adapter. This allows the distal end 51 of the adapter 42A to flex as required during scraping. The length of insertion into the internal chamber 54 of the adapter 42A is preferably set to securely fit the adapter 42A onto the tip 33 while maintaining flexibility for scraping.

Figure 1B:
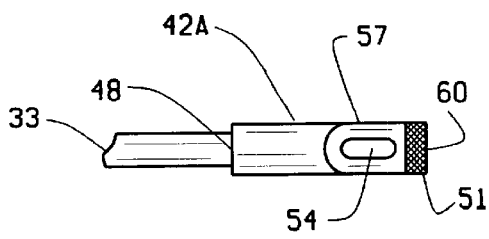
FIG. 1B is an enlarged, partial view of an embodiment of an adapter for the infusion/aspirating membrane scraper of FIG. 1A.
Figure 1C:
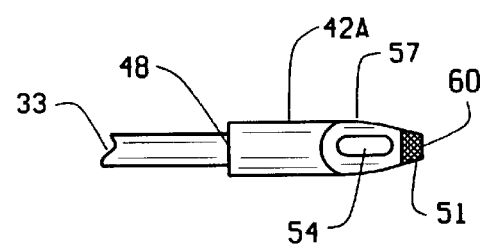
FIG. 1C is an enlarged, partial view of a second embodiment of an adapter for the infusion/aspirating membrane scraper of FIG. 1A.

The distal end 51 of the adapter 42A has a curved beveled surface 57 that exposes the internal chamber 54 of the adapter. This is best shown in FIGS. 1B and 1C. The curved open surface optimizes delivery of aspiration or infusion sources. This bevel surface 57 also provides better visualization of the surgical site and increased flexibility for scraping with the distal edge 51. The adapter distal end 51 can be configured in a flat arrangement as shown in FIG. 1B or tapered arrangement as shown in FIG. 1C to facilitate fluid manipulation around the surface of the retina.

As shown in FIGS. 1B and 1C, the distal end 51 of the adapter has abrasive particles 60 adhered thereon. The film of abrasive particles 60 in the preferred embodiment consists of synthetically-made diamond particles. Other similar types of particles and other types of abrasive surfaces may be employed. The particles may be arranged in a film that is bonded to the adapter 42A such that the particles are not loosened and disassociated from the film and the distal end 51 of the adapter during the scraping operation. Preferably, the adapter 42A is made from a flexible, biologically inert rubber or other similar material that is compatible with the bonding methods used for the chosen abrasive particles. The film of abrasive particles 60 is bonded to the distal end 51 of the adapter such that all exposed edges of the distal end 51 of the adapted are coated while the distal end 51 of the adapter is maintained in communication with the internal chamber 54. In the axial direction of the adapter 42A, the abrasive particles are preferably attached 1 mm to 2 mm back from the distal end 51. The particles adhered to the distal end 51 may be chosen for their coarseness and texture to create the desired effect for membrane scraping and removal rates. As shown in FIG. 1A, an external infusion/aspiration source 27 may be interfaced at the taper 24 in the internal passage 21 of the instrument handle 13 and directed into the hollow core 45 of the tip, into the internal chamber 54 of the adapter, and through the bevel surface 57.

Figure 2:
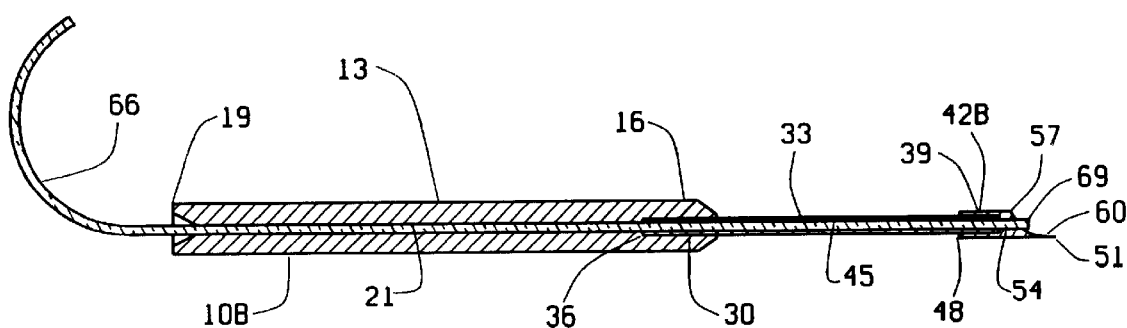
FIG. 2 is a cross sectional view of a second embodiment of the current invention, an illuminated membrane scraper.

In FIG. 2, a similar embodiment of the apparatus of the invention shown in FIG. 1A is depicted. In this embodiment, the microsurgical instrument 10B is an illuminated membrane scraper. The instrument handle 13, adapter 42B, and tip 33 are constructed much in the same way as previously mentioned. The differences between the two embodiments will be discussed to avoid repetition of the same features and modes of operation. As shown in FIG. 2, the illuminated microsurgical instrument 10B contains an optical fiber 66 that is directed through the internal passage 21 of the instrument handle, into the hollow core 45 in the tip, and through the internal chamber 54 in the adapter 42B. In this configuration, the instrument handle 13 is configured slightly different than shown in FIG. 1A with the outwardly conical shaped taper 24 omitted from the proximal end 19 of the instrument handle. Preferably, the distal end 16 of the instrument handle contains the same counter-bore 30 into which the proximal end 36 of the tip is securely press fit.

Preferably, the optical fiber 66 is directed through the internal passage 21 of the instrument handle through the hollow core 45 of the tip to the internal chamber 54 of the adapter. The portion of the optic fiber 66 outside the instrument is covered with a protective cladding and the portion of the optic fiber that enters the instrument has had its cladding removed. The adapter 42B is positioned on the distal end 39 of the tip. The optical fiber 66 may be made from glass or plastic, as is common in the art. Preferably, the adapter 42B is made from a translucent, inert, elastic material, which will glow and provide illumination of the surgical site when the optical fiber 66 is illuminated. The adapter 42B contains the same bevel surface 57 across the internal chamber 54 of the adapter as shown in FIG. 1B and FIG. 1C. In this application, the bevel surface 57 has an additional design consideration in that the surface 57 is made in a manner so as to provide a desired illumination pattern for the surgical site. The distal end 69 of the optical fiber slightly protrudes from the hole created by the bevel surface 57 across the internal chamber 54 in the adapter. The distal end 69 of the optical fiber 66 may also be shaped to create the desired illumination pattern at the surgical site. For example, the distal end 69 of the optical fiber 66 may be rounded.

Figure 3A:
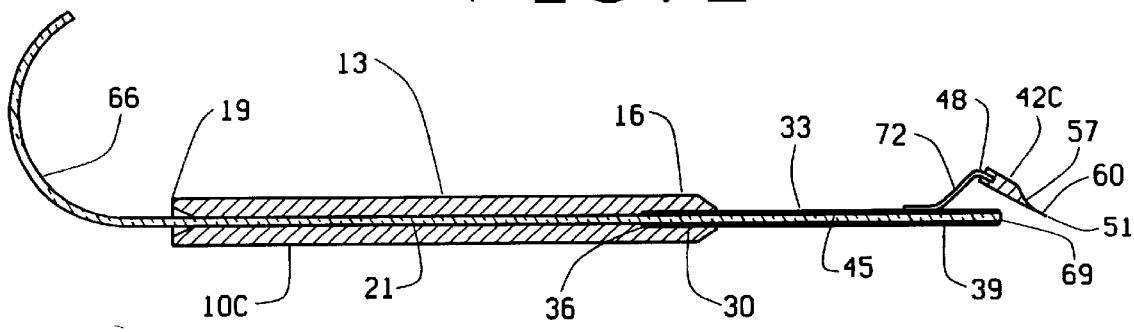
FIG. 3A is a cross sectional view of a third embodiment of the present invention, an illuminated membrane scraper.

In FIG. 3A, an illuminated membrane scraper 10C is shown. In this embodiment, the construction is very similar to the device shown in FIG. 2 in that the instrument handle 13 is adapted to accept an optical fiber 66 running through the internal passage 21 in the instrument handle. The tip 33 is press fit and adhered in the counter-bore 30 on the distal end 16 of the instrument handle. However, in this embodiment the adapter 42C is moved to a location where it is positioned above the distal end 39 of the tip by a bracket 72. The bracket 72 is preferably made of a surgical grade steel wire or resilient plastic and is attached to the distal end 39 of the tip. The bracket 72 positions the adapter 42 at an acute angle with the tip 33. The acute angle is chosen to hold the adapter 42 away from the distal end 39 of the tip such that the optical fiber 66 can effectively illuminate the distal end 51 of the adapter and the surgical site. The bracket 72 holds the adapter 42 at the acute angle such that the distal end 51 of the adapter intersects the path of illumination while preserving an overall low cross section for the microsurgical instrument 10 that permits introduction into a straight cannula.

In this embodiment of the invention, the adapter 42C may be provided with an internal chamber 54 similar to the adapters shown in FIGS. 1A, 1B, 1C, and 2. In this configuration, the bracket 72 may be inserted into the internal chamber 54 of the adapter 42C in a manner similar to the arrangement of the tip and the adapter described previously. The bracket may penetrate the internal chamber 54 of the adapter 42C to a depth that preserves the flexibility of the adapter 42C for scraping while maintaining a secure fit on the bracket 72. However, the adapter also may be a solid member with no internal chamber and the bracket may be pressed into the proximal end of the adapter and adhered thereto.

Figure 3B:
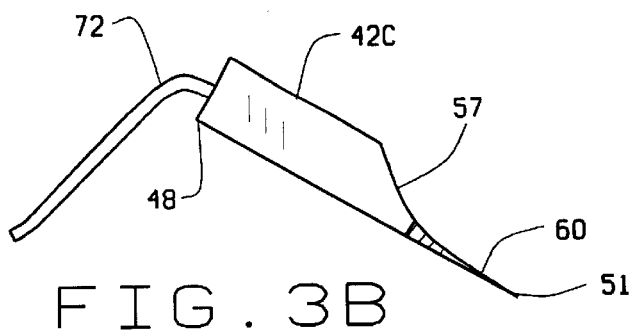
FIG. 3B is a enlarged, partial view of the adapter used on the illuminated membrane scraper of FIG. 3A.

As shown in FIG. 3A, the distal end 69 of the optical fiber protrudes from the hollow core 45 of the tip. The distal end 69 of the optical fiber is shaped to provide the desired illumination pattern at the surgical site. As shown in FIG. 3B, the adapter 42C also has abrasive particles 60 bonded to its distal end 51. With this arrangement of the microsurgical instrument 10C, the surgeon may scrape the membranes while directly illuminating the surgical site.

Figure 4A:
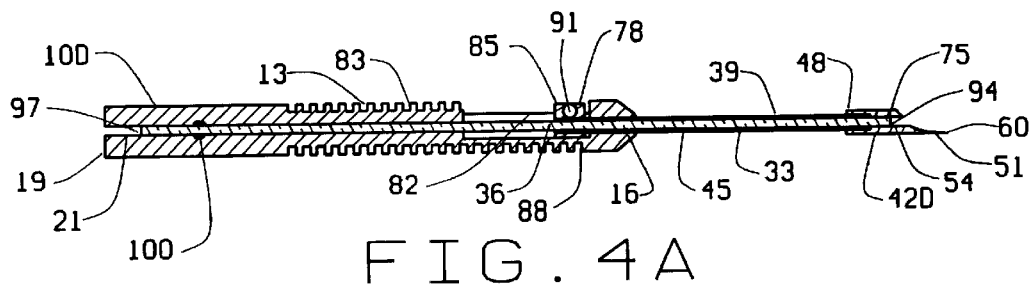
FIG. 4A is a cross sectional view of a fourth embodiment of the present invention, a membrane scraper with adjustable stiffness pick, the pick shown in a retracted position.
Figure 4B:
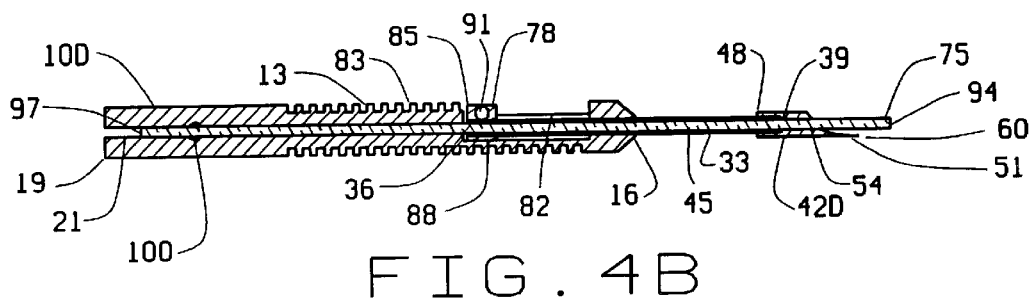
FIG. 4B is a cross sectional view of the membrane scraper with adjustable stiffness pick of FIG. 4A, the pick shown in an extended position.

FIGS. 4A and 4B show another embodiment of the present invention, a membrane scraper 10D with an adjustable stiffness pick 75. The microsurgical instrument has the construction of an instrument handle 13 with tip 33 and adapter 42D as previously described. In the embodiment shown in FIGS. 4A and 4B, the microsurgical instrument 10D has an adjustable pick 75 received in the internal passage 21 of the instrument handle 13, the hollow core 45 of the tip 33, and in the internal chamber 54 of the adapter 42D. This pick 75 is secured in the handle passage 21 by a set screw (not shown) or by other equivalent means. The length of the pick 75 exposed from the bevel section cut of the adapter 42D may be varied between an extended position in which the pick 75 is exposed from the distal end 51 of the adapter 42D and a retracted position in which the pick 75 is retracted into the hollow core 45 of the tip 33. The length of the pick 75 exposed from the adapter controls the relative stiffness of the pick 75. When a longer length of the pick 75 is exposed from the distal end 51 of the adapter 42D, the pick 75 is more flexible and less stiff. As the pick 75 is retracted, the pick 75 becomes stiffer.

To adjust the stiffness in the pick 75, the instrument handle 13 is constructed with a slide mechanism 78 located in an axial slot 82 cut in the outer cylindrical wall of the instrument handle 13. The axial slot 82 provides communication between the outer surface of the cylindrical wall of the instrument handle 13 and the internal passage 21 of the instrument handle. To aid the surgeon in manipulating the slide mechanism 78, a grip 83 may be formed on the exterior of the cylinder wall of the instrument handle 13. Additionally, the diameter of the internal passage 21 in the distal end portion 16 of the instrument handle is increased to allow the tip 33 to slide freely through the distal end 16 portion of the instrument handle 13.

The slide mechanism 78 preferably includes a finger pad 85 connected to the proximal end 36 of the tip 33. The finger pad 85 is positioned in the axial slot 82 for axial sliding movement of the finger pad 85 through the axial slot 82 between a pushed forward position of the finger pad and a pulled back position of the finger pad. The finger pad 85 is preferably constructed of the same material as the instrument handle 13, a disposable medical grade plastic. The proximal end 36 of the tip 33 is received at the distal end 16 of the instrument handle 13 and positioned in the axial slot 82 in the instrument handle 13.

Preferably, the finger pad 85 has a hole 88 into which the proximal end 36 of the tip is inserted. A set screw 91 may then be used to secure the finger pad 85 to the proximal end 36 of the tip. Thus, moving the finger pad 85 to its pushed forward position will also move the tip 33 through the distal end 16 portion of the instrument handle to its forward most position or pushed forward position relative to the instrument handle 13 where the distal end 39 of the tip 33 projects its greatest distance from the instrument handle distal end 16. Moving the finger pad 85 to its pulled back position will also move the tip 33 to its pulled back position relative to the instrument handle 13 where the tip distal end 39 projects its shortest distance from the instrument handle distal end 16. In the preferred embodiment of the invention, the travel distance of the finger pad in the axial slot 82 and of the tip distal end 39 is 25 mm.

As shown in FIGS. 4A and 4B, a medical grade plastic pick 75 having distal 94 and proximal 97 ends is directed from the bevel surface 57 across the internal chamber 54 of the adapter, into the hollow core 45 of the tip and into a portion of the instrument handle internal passage 21. The overall length of the pick 75 is preferably slightly larger than the combined length of the tip 33 and the adapter 42. The pick 75 is preferably positioned in the internal chamber 54 of the adapter, the hollow core 45 of the tip, and the instrument handle internal passage 21 so that the distal end 94 of the pick is positioned just inside the adapter proximal end 48 when the tip 33 and adapter 42 are moved to their forward most positions.

As shown in FIG. 4A, the pick 75 preferably passes through the axial slot 82 in the side of the instrument handle 13 and extends for a short distance through the internal passage 21 of the instrument handle behind the terminal point of the axial slot 82. The pick proximal end 97 is preferably secured stationary relative to the instrument handle 13 by a set screw that passes through the side of the instrument handle 13 and engages against the exterior of the pick 75. With the pick distal end 94 being positioned just inside the proximal end 48 of the adapter when the tip 33 and adapter 42D are moved to their pushed forward positions as shown in FIG. 4A, a distal end 94 portion of the pick projects from the adapter distal end 51 when the finger pad 85, and the tip 33 and adapter 42D are moved to their pulled back positions as shown in FIG. 4B. The distal end 94 portion of the pick that projects from the adapter distal end 51 is shown in FIG. 4B. This distal end 94 portion has a variable stiffness as the length of the pick 75 exposed from the bevel surface 57 in the adapter is adjusted. As the length of pick 75 is increased, the relative stiffness of the pick 75 is decreased. As the pick 75 is drawn into the bevel surface 57 in the adapter 42D as the finger pad 85 is moved to its pushed forward position as shown in FIG. 4A, the relative stiffness of the pick 75 increases.

In a like manner, the position of the pick distal end 94 inside the adapter 42D adjusts the stiffness of the adapter 42D. In the previous embodiments of the invention, the stiffness of the adapter was controlled by the adapter's material and dimensions, the bevel surface, and the depth of penetration of the tip into the adapter or by the bracket into the adapter. With the pick distal end positioned in the adapter adjacent the adapter distal end, the pick may also serve to stiffen the adapter. Retracting the pick toward the adapter proximal end reduces the stiffness of the adapter. The combined action of the pick 75 and the abrasive particles 60 in the distal end 51 of the adapter 42D, allow the surgeon to better control the rate of membrane removal while giving the flexibility to either use the film of abrasive particles 60 or the pick 75 for actual removal.

To assist the sliding of the tip 33 over the distal end 94 portion of the pick, the hollow core 45 of the tip is preferably coated with a layer of a sliding material such as Teflon®. The Teflon® layer preferably extends only a short distance in the hollow core 45 of the tip adjacent the tip distal end 39. The remainder of the hollow core 45 of the tip may be dimensioned slightly larger than the exterior diameter of the pick 75 providing an air gap between the pick exterior and the hollow core 45 of the tip that reduces actuation drag and enhances the ease of sliding the tip 33 over the exterior of the pick 75.

It is not the intention of this invention to limit the configuration of this embodiment to where the pick is stationary and the tip and adapter move relative to the pick. It is also possible to move the pick in relation to the tip and adapter to achieve the stiffness required to effectively scrape membranes.

Figure 5A:
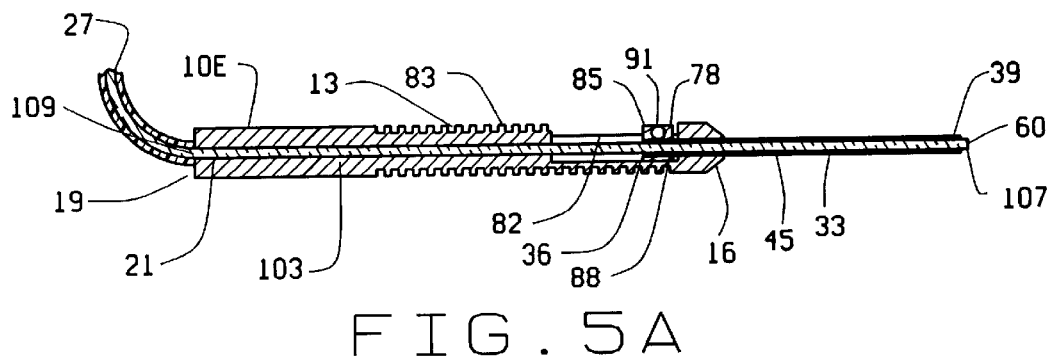
FIG. 5A is a cross sectional view of a fifth embodiment of the present invention, a directional endoscopic abrasive membrane scraper connected to an external aspiration source, a tip shown in a retracted position.
Figure 5B:
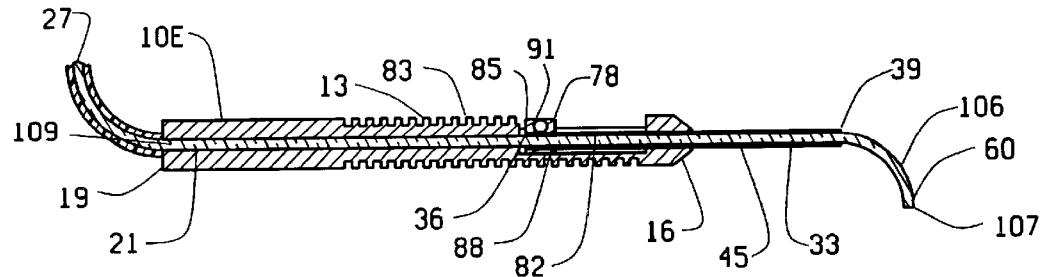
FIG. 5B is a cross sectional view of the directional endoscopic abrasive membrane scraper of FIG. 5A, a tip shown in an extended position.

In FIGS. 5A and 5B, the embodiment of the apparatus of the invention is shown where the pick of FIGS. 4A and 4B is replaced with a tube 103 and the adapter is removed from the distal end 39 of the tip. In this configuration, the embodiment of the microsurgical instrument 10E in FIGS. 5A and 5B is termed a directional endoscopic abrasive aspiration membrane scraper. In this embodiment, the instrument handle 13 is configured much as it was in the FIGS. 4A and 4B. The internal passage 21 is provided in the instrument handle 13 and the distal end 16 portion of the instrument handle is adapted for sliding motion of the tip 33 therethrough into the axial slot 82. The instrument handle is preferably configured with a grip 83 to allow the surgeon to manipulate the sliding mechanism 78. The instrument handle 13 contains an axial slot 82 in the outer cylindrical wall located toward the distal end 16 of the instrument handle 13 for locating the sliding mechanism 78. A finger pad 85 is preferably inserted into the axial slot 82. The finger pad 85 has a hole 88 into which the proximal end of the tip is inserted. The set screw 91 preferably secures the finger pad 85 to the proximal end 36 of the tip. Thus, moving the finger pad 85 to its pushed forward position will also move the tip 33 through the distal end 16 portion of the instrument handle to its forward most position or pushed forward position relative to the handle where the distal end 39 of the tip projects its greatest distance from the instrument handle distal end 16. Moving the finger pad 85 to its pulled back position will also move the tip 33 to its pulled back position relative to the instrument handle 13 where the tip distal end 39 projects its shortest distance from the instrument handle distal end 16. In the preferred embodiment of the invention, the travel distance of the finger pad 85 in the slot 82 and the tip distal end 39 is 25 mm.

Located in the internal passage 21 of the instrument handle is the tube 103 with a pre-formed bend 106 on its distal end 107. Preferably, the tube is constructed of nitinol. The proximal end 109 of the tube is directed into and through the hollow core 45 of the tip, and into the internal passage 21 of the instrument handle. The proximal end 109 of the tube 103 may be connected to an aspiration or infusion source 27. A distal end 107 portion of the tube is pre-formed with a bend 106 through a 90° angle relative to the distal end 39 of the tip. Around the distal end 107 of the tube, the abrasive particles 60 are deposited, covering the exterior of the cylindrical portion of the tube 103 back 1 mm to 2 mm from the distal end 107 of the tube as well as the circumferential annular edge at the distal end of the tube 107.

As shown in FIG. 5A, when the finger pad 85 on the instrument handle 13 is pushed forward, it extends the tip 33 to its pushed forward position in which the distal end portion of the tube 107 is completely contained inside the hollow core 45 of the tip and is held in the straight configuration of the hollow core 45 of the tip. As shown in FIG. 5B, when the finger pad 85 is moved to its pulled back position, the tip 33 is also moved back to its pulled back position causing the bend portion 106 of the distal end 107 of the tube contained therein to be gradually exposed at the distal end of the tip 39. As the tube 103 is exposed at the distal end of the tip 39, the tube 103 gradually bends from the initial straight configuration of the tip 33 toward the 90° pre-bent configuration of the tube 103. In this manner, the tube 103 may be adjustably positioned through any angle between 0° when the tube 103 is entirely contained in the tip 33 at its pushed forward position, to a 90° bend when the tube 103 projects from the tip distal end 39 with the tip 33 moved to its pulled back position.

In use of the directional membrane scraper in the scraping of obscured retinal membranes, the finger pad 85 is moved to its pushed forward position. The tube 103 is contained in the tip 33, which projects in a straight line from the distal end 16 of the instrument handle. The tip 33 is then inserted through a cannula positioned in an incision in the eye. The finger pad 85 is then slowly moved toward the rear of the instrument handle 13 causing the tip 33 to slowly move toward its pulled back position relative to the instrument handle 13. This, in turn, causes the pre-bent 106 distal end 107 portion of the tube to gradually bend from its straight configuration toward its 90° configuration. The bending of the tube 103 allows optimal positioning of the film of abrasive particles 60 to areas where a straight scraping adapter 42 shown in the embodiments of FIGS. 1, 2, 3, and 4 may not reach. Rotation of the entire instrument about its center axis may be necessary to further direct the tube. Once the proper location of the distal tube is achieved, the surgeon may begin scraping and treating the surgical site with aspiration/infusion functions supplied via the tube. Retraction of the tip 33 is performed by first pushing the finger pad 85 forward causing the tip 33 to move toward its pushed forward position and causing straightening of the bent portion 106 of the tube projecting from the tip 33. With the tube 103 contained in the tip 33, the tip 33 is then pulled back through the surgical entry site.

In alternate embodiments of the invention, the actuation mechanism provided by the finger pad may be replaced with other types of mechanisms that would produce the same axial movement of the tip, for example by a trigger mechanism manipulated by the surgeon's finger or by a squeeze mechanism that is squeezed by the surgeon's hand. In addition, a fiducial mark may be provided on the tip adjacent its distal end to indicate to the surgeon which direction the distal end portion of the tube will bend as it is extended out of the distal end of the tip. This would be useful to the surgeon in accurately positioning the tip in the interior of the eye before the bending movement of the tube is commenced.

The intent of this embodiment of the invention is not only to work in the intraocular cavity, this microsurgical tool may be used in operations where the treatment tool must be inserted into a cavity where the spatial arrangement of the cavity obscures treatment surfaces, for example, in brain tumor removal.

While the present invention has been described by reference to specific embodiments, it should be understood that modifications and variations of the invention may be constructed without departing from the scope of the invention defined in the following claims.

What is claimed is:

1. A surgical tool comprising:

an instrument having a tubular length with opposite first and second ends and an internal passage extending through the instrument between the first and second ends, the instrument includes an elongate handle with opposite proximal and distal ends and an elongate tubular tip with opposite proximal and distal ends, the tip projects from the handle and the internal passage extends through the handle and tip from a handle opening at the handle proximal end to a tip opening at the tip distal end;

an optic fiber extends through the instrument internal passage in the handle and in the tip; and, an abrasive surface is provided on the tip distal end and is spaced from the tip opening.

2. The tool of claim 1, wherein:

An adapter is provided on the tip distal end and projects away from the tip to a distal end of the adapter, the abrasive surface is on the distal end of the adapter; and the distal end of the adapter is flexible.

3. The tool of claim 1, wherein:

An adapter is provided on the tip distal end and projects away from the tip to a distal end of the adapter, the abrasive surface is on the distal end of the adapter; and the adapter has an internal chamber and a hole that communicates with the internal chamber, and the internal chamber communicates with the instrument internal passage.

4. The tool of claim 3, wherein:

the optic fiber extends through the adapter internal chamber.

5. The tool of claim 1, wherein:

An adapter is provided on the tip distal end and projects away from the tip to a distal end of the adapter, the abrasive surface is on the distal end of the adapter; and the abrasive surface is comprised of abrasive particles on the distal end of the adapter.

6. The tool of claim 3, wherein:

a hollow tube extends through the instrument internal passage and the adapter internal chamber.

7. The tool of claim 3, wherein:

the adapter distal end has a beveled surface and the hole passes through the beveled surface and the abrasive surface is on the beveled surface.

8. The tool of claim 1, wherein:

An adapter is provided on the tip distal end and projects away from the tip to a distal end of the adapter, the abrasive surface is on the distal end of the adapter; and a bracket is mounted on the second end of the instrument and extends at an angle from the instrument and the adapter is mounted to the bracket.

9. The tool of claim 1, wherein:

the proximal end of the tip is mounted to the distal end of the handle and the adapter is on the distal end of the tip.

10. The tool of claim 9, wherein:

the tip is mounted to the handle for movement of the tip between extended and retracted positions of the tip relative to the handle and the adapter moves with the tip between the extended and retracted positions.

11. The tool of claim 10, wherein:

the optic fiber has a distal end that is positioned in the tip adjacent the tip distal end when the tip is in the extended position relative to the handle, and the optic fiber distal end projects from the tip distal end when the tip is in the retracted position relative to the handle.

12. The tool of claim 10, wherein:

a hollow tube extends through the instrument internal passage through the handle and the tip, the tube has a distal end that is positioned in the tip adjacent the tip distal end when the tip is in the extended position relative to the handle, and the tube distal end projects from the tip distal end when the tip is in the retracted position relative to the handle.

13. The tool of claim 12, wherein:

the tube distal end has a resilient bend that causes the tube distal end to bend through an angle relative to the tip when the tube distal end projects from the tip distal end when the tip is in the retracted position relative to the handle and causes the tube distal end to straighten out when the tube distal end is positioned in the tip when the tip is in the extended position relative to the handle.

14. A surgical tool comprising:

an instrument having a tubular length with opposite first and second ends and an internal passage extending through the instrument between the first and second ends, the instrument includes an elongate handle with opposite proximal and distal ends and an elongate tubular tip with opposite proximal and distal ends, the proximal end of the tip is mounted to the distal end of the handle, the instrument internal passage extends through the handle and the tip;

an optic fiber extends through the instrument internal passage in the handle and in the tip; and, an abrasive surface is provided on the tip distal end.

15. The tool of claim 14, wherein:

the instrument has an opening at the second end that communicates with the internal passage and the abrasive surface is adjacent the opening.

16. The tool of claim 14, wherein:

the abrasive surface is comprised of abrasive particles.

17. The tool of claim 15, wherein:

the optic fiber has a distal end positioned adjacent the opening at the instrument second end and an opposite proximal end that is remote from instrument.

18. The tool of claim 15, wherein:

a hollow tube extends through the instrument internal passage, the hollow tube has a distal end positioned adjacent the opening at the instrument second end and an opposite proximal end that is remote from the instrument.

19. The tool of claim 14, wherein:

an adapter is on the distal end of the tip and the abrasive surface is on the adapter.

20. The tool of claim 14, wherein:

an adapter is mounted on the second end of the instrument, the adapter has a flexible distal end that projects away from the instrument and the abrasive surface is on the adapter distal end.

* * * * *